United States Patent
Van Den Berg et al.

(10) Patent No.: US 8,083,815 B2
(45) Date of Patent: Dec. 27, 2011

(54) PROCESS TO PREPARE METHANOL AND/OR DIMETHYLETHER

(75) Inventors: Robert Van Den Berg, Amsterdam (NL); Leslie Andrew Chewter, Amsterdam (NL); Jeroen Van Westrenen, Amsterdam (NL); Ferry Winter, Amsterdam (NL)

(73) Assignee: Shell Oil Company, Houston, TX (US)

( * ) Notice: Subject to any disclaimer, the term of this patent is extended or adjusted under 35 U.S.C. 154(b) by 488 days.

(21) Appl. No.: 12/356,396

(22) Filed: Jan. 20, 2009

(65) Prior Publication Data
US 2009/0126259 A1    May 21, 2009

Related U.S. Application Data

(60) Provisional application No. 61/140,648, filed on Dec. 24, 2008.

(30) Foreign Application Priority Data
Dec. 22, 2008 (EP) .................................... 08172609

(51) Int. Cl.
*C10L 5/00* (2006.01)
(52) U.S. Cl. ........................... 44/620; 568/671; 568/910
(58) Field of Classification Search .................... 44/620; 568/671, 910
See application file for complete search history.

(56) References Cited

U.S. PATENT DOCUMENTS

| | | | | |
|---|---|---|---|---|
| 4,076,796 A | 2/1978 | Reh et al. | ...................... | 423/659 |
| 4,076,842 A | 2/1978 | Plank et al. | .................... | 423/328 |
| 4,397,827 A | 8/1983 | Chu | ............................. | 423/326 |
| 4,430,444 A | 2/1984 | Reichl | ........................... | 518/703 |
| 4,510,874 A | 4/1985 | Hasenack | ..................... | 110/347 |
| 4,523,529 A | 6/1985 | Poll | ............................. | 110/263 |
| 4,556,477 A | 12/1985 | Dwyer | ......................... | 208/111 |
| 4,590,320 A | 5/1986 | Sapre | ........................... | 585/324 |
| 4,665,249 A | 5/1987 | Mao et al. | ..................... | 585/408 |
| 4,836,146 A | 6/1989 | Russell et al. | ................ | 122/379 |
| 4,887,962 A | 12/1989 | Hasenack et al. | ............ | 110/263 |

(Continued)

FOREIGN PATENT DOCUMENTS
DE      2610982       9/1977

(Continued)

OTHER PUBLICATIONS

Weissesrmehl, K. et al., Industrial Organic Chemistry, 3$^{rd}$ Edition, Wiley 1997, pp. 13-28.

(Continued)

*Primary Examiner* — Cephia D Toomer

(57) ABSTRACT

A process to prepare methanol and/or dimethylether from a solid carbonaceous feedstock comprising the steps of
(a) feeding an oxygen-comprising gas and the carbonaceous feedstock to a burner firing into a reactor vessel,
(b) performing a partial oxidation of the carbonaceous feedstock in said burner to obtain a stream of hot synthesis gas and a liquid slag whereby both the hot synthesis gas and the liquid slag flow downwardly relative to the burner,
(c) cooling the hot synthesis gas by direct contact with a liquid water-containing cooling medium,
(d) performing a water shift reaction on at least part of the synthesis gas, to obtain a synthesis gas effluent,
(e) performing an oxygenate synthesis using the synthesis gas effluent of step (d), to obtain a methanol and/or dimethylether containing oxygenate effluent and a first liquid water-rich by-product,
wherein at least part of the first liquid water-rich by-product is used in step (c), forming at least part of the liquid water-containing cooling medium.

14 Claims, 3 Drawing Sheets

U.S. PATENT DOCUMENTS

| | | | | |
|---|---|---|---|---|
| 5,037,511 | A | 8/1991 | Dornhagen et al. | 203/37 |
| 5,254,596 | A * | 10/1993 | Irick et al. | 518/728 |
| 5,367,100 | A | 11/1994 | Gongwei et al. | 585/640 |
| 5,714,662 | A | 2/1998 | Vora et al. | 585/640 |
| 5,817,906 | A | 10/1998 | Marker et al. | 585/640 |
| 6,046,372 | A | 4/2000 | Brown et al. | 585/640 |
| 6,248,795 | B1 * | 6/2001 | Jun et al. | 518/713 |
| 6,791,002 | B1 | 9/2004 | Abrevaya et al. | 585/648 |
| 6,797,851 | B2 | 9/2004 | Martens et al. | 585/640 |
| 2003/0078463 | A1 | 4/2003 | Martens et al. | 585/638 |
| 2004/0122267 | A1 | 6/2004 | Sher et al. | 585/324 |
| 2006/0020155 | A1 | 1/2006 | Beech, Jr. et al. | 585/639 |
| 2006/0135834 | A1 | 6/2006 | Xu et al. | 585/639 |
| 2007/0155999 | A1 | 7/2007 | Pujado et al. | 585/327 |
| 2007/0203380 | A1 | 8/2007 | Vora et al. | 585/638 |
| 2008/0182912 | A1 | 7/2008 | Van Den Berg et al. | 518/719 |
| 2009/0105429 | A1 | 4/2009 | Chewter et al. | 526/67 |
| 2009/0259076 | A1 * | 10/2009 | Simmons et al. | 568/671 |

FOREIGN PATENT DOCUMENTS

| | | | |
|---|---|---|---|
| DE | 4336790 | | 5/1995 |
| DE | 10027159 | | 12/2001 |
| DE | 10043544 | | 3/2002 |
| EP | 0088494 | | 1/1983 |
| EP | 0340576 | | 11/1989 |
| EP | 0343454 | | 11/1989 |
| EP | 400740 | | 5/1990 |
| EP | 416242 | | 3/1991 |
| EP | 0444684 | | 9/1991 |
| EP | 0485145 | | 11/1991 |
| EP | 0489497 | | 11/1991 |
| EP | 551951 | | 1/1993 |
| EP | 662506 | | 7/1995 |
| EP | 1923380 | * | 5/2008 |
| GB | 2233664 | | 1/1991 |
| WO | WO9522516 | | 8/1995 |
| WO | WO0121736 | | 3/2001 |
| WO | WO0129152 | | 4/2001 |
| WO | WO0162689 | | 8/2001 |
| WO | WO0185872 | | 11/2001 |
| WO | WO02085788 | | 10/2002 |
| WO | WO03020667 | | 3/2003 |
| WO | WO03080221 | | 10/2003 |
| WO | WO2004005438 | | 1/2004 |
| WO | WO2004018089 | | 3/2004 |
| WO | WO2004031327 | | 4/2004 |
| WO | WO2004037950 | | 5/2004 |
| WO | WO2004056944 | | 7/2004 |
| WO | WO2006020083 | | 2/2006 |
| WO | WO2006070018 | | 7/2006 |
| WO | WO2006117335 | | 11/2006 |
| WO | WO2006117355 | | 11/2006 |
| WO | WO2007135052 | | 11/2007 |

OTHER PUBLICATIONS

Ch. Baerlocher, et al., Database of Zeolite Structures, http://www.iza-structure.org/databases/ date unknown.

An, W., et al., Dehydration of Methanol to Dimethyl Ether by Catalytic Distillation, The Canadian Journal of Chem. Eng., vol. 82, Aug. 2004, pp. 948-955.

* cited by examiner

PROCESS TO PREPARE METHANOL AND/OR DIMETHYLETHER

This patent application claims the benefit of European patent application No. 08172609.3, filed Dec. 22, 2008 and U.S. Provisional Application 61/140,648, filed Dec. 24, 2008, both of which are incorporated herein by reference.

FIELD OF THE INVENTION

The present invention relates to improvements relating to a solid carbonaceous feed to a methanol and/or dimethylether process.

BACKGROUND OF THE INVENTION

Methanol and dimethylether are useful feedstocks for preparing olefins in so-called oxygenate-to-olefins processes or as feedstock for preparing gasoline in a so-called oxygenate-to-gasoline process. Such an oxygenate-to-olefins process can convert methanol and/or dimethylether over a catalyst to a product stream that is typically rich in lower olefins, including ethene, propene, as well as butenes, pentenes, hexenes, and also higher olefins and other hydrocarbons and some by-products. The oxygenate feedstock can be obtained from synthesis gas, also referred to as syngas.

WO-A-2006020083 describes a process wherein synthesis gas is converted in a first step to methanol and in a second step to dimethylether. Water-containing oxygenates are formed in both the first and second reaction steps of the known process. A water removal unit serves for separating residual oxygenate components such as residual dimethylether and residual methanol from the water received therein. Wastewater streams obtained in the known process are preferably directed to a water treatment facility.

The separation of water-containing minimum concentrations of methanol and dimethylether from the effluents of the reaction contributes significantly to the cost and overall complexity of the process. There exists a desire to obtain a more simple process.

SUMMARY OF THE INVENTION

In accordance with the invention there is provided a process to prepare methanol and/or dimethylether from a solid carbonaceous feedstock comprising the steps of
(a) feeding an oxygen-comprising gas and the carbonaceous feedstock to a burner firing into a reactor vessel,
(b) performing a partial oxidation of the carbonaceous feedstock in said burner to obtain a stream of hot synthesis gas and a liquid slag whereby both the hot synthesis gas and the liquid slag flow downwardly relative to the burner,
(c) cooling the hot synthesis gas by direct contact with a liquid water-containing cooling medium,
(d) performing a water shift reaction on at least part of the synthesis gas, to obtain a synthesis gas effluent,
(e) performing an oxygenate synthesis using the synthesis gas effluent of step (d), to obtain a methanol and/or dimethylether-containing oxygenate effluent and a first liquid water-rich by-product,
wherein at least part of the first liquid water-rich by-product is used in step (c), forming at least part of the liquid water-containing cooling medium.

An advantage of the claimed process is that it is not needed to perform a sophisticated separation of methanol from the liquid water-rich by-product. By recycling these components with the water as cooling medium they can remain in the overall process as such, thereby improving the overall efficiency. Depending on the temperature of the synthesis gas in step (c) part or all of the methanol and/or dimethylether may be converted into hydrogen and carbon monoxide and form part of the synthesis gas.

DETAILED DESCRIPTION OF THE INVENTION

Figure 1:
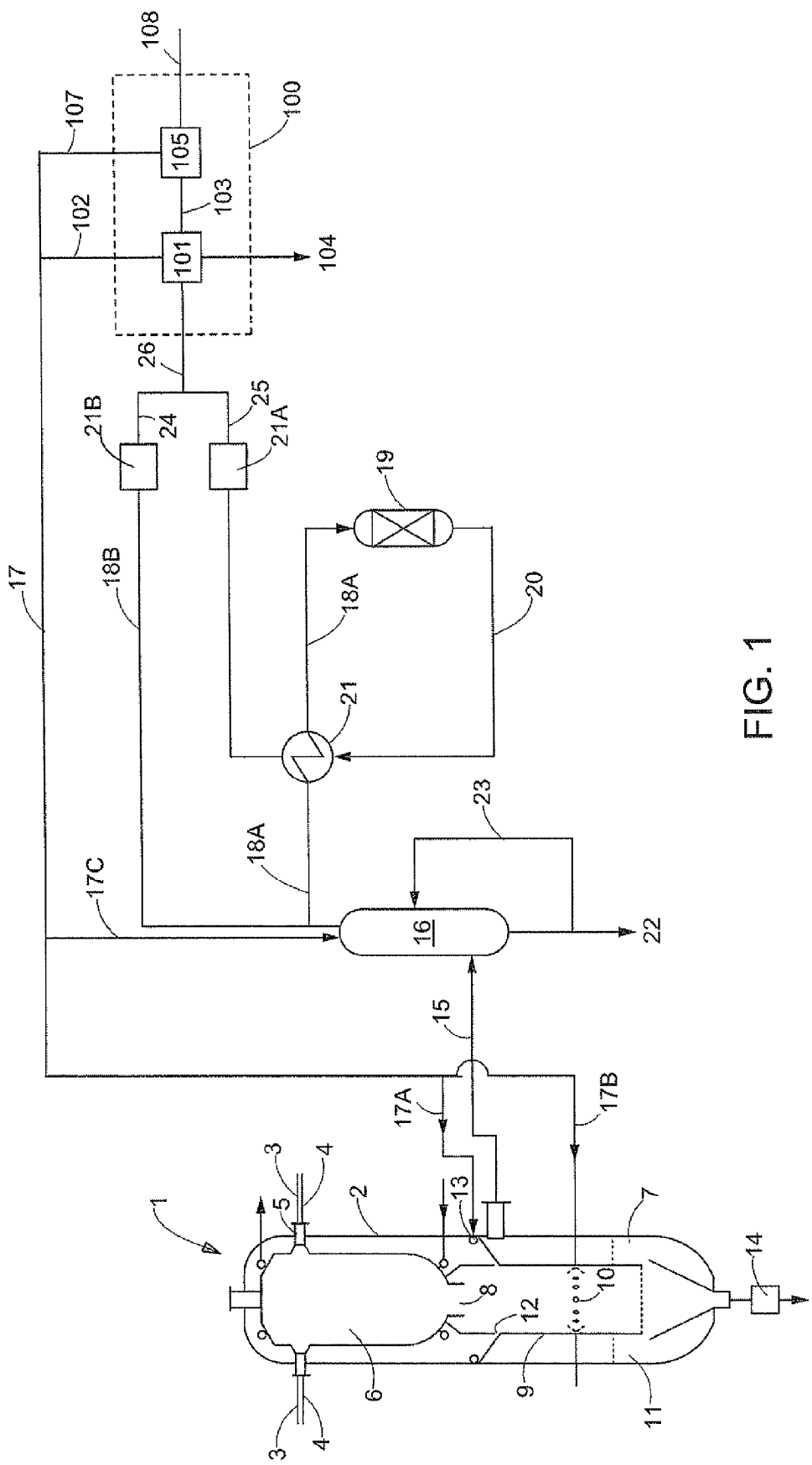
FIG. 1 shows schematically a process scheme for performing a method according the present invention.

Synthesis gas is a gas comprising carbon monoxide (CO), hydrogen ($H_2$) and optionally carbon dioxide ($CO_2$). Optionally, synthesis gas may also include methane ($CH_4$), ethane, propane, heavier hydrocarbons, or other compounds. A particularly interesting source of synthesis gas is from the gasification of a solid carbonaceous feedstock such as coal.

Preferred solid carbonaceous feeds as used in step (a) are ash and sulphur containing feedstocks, preferably coal, biomass, for example wood, in particular torrefied wood, and waste. More preferably the solid carbonaceous feed is substantially (i.e. >90 wt. %) comprised of naturally occurring coal or synthetic (petroleum)cokes, most preferably coal. Suitable coals include lignite, bituminous coal, sub-bituminous coal, anthracite coal, and brown coal.

In step (a) an oxygen-comprising gas and the carbonaceous feedstock are fed to a burner firing into a reactor vessel. In step (b) a partial oxidation of the carbonaceous feedstock in said burner is performed to obtain a stream of hot synthesis gas. This stream of hot synthesis gas flows downwards relative to the burner and a liquid slag flows downwards relative to the burner. The partial oxidation is carried out by partially combusting the carbonaceous feed with a limited volume of oxygen at a temperature normally between 800° C. and 2000° C., preferably between 1400 and 1800° C., at a pressure between 20 and 100 bar, and preferably in the absence of a catalyst.

The gasification is preferably carried out in the presence of oxygen-comprising gas and optionally some steam, the purity of the oxygen-comprising gas preferably being at least 90% by volume, nitrogen, carbon dioxide and argon being permissible as impurities. Substantially pure oxygen is preferred, such as prepared by an air separation unit (ASU). The oxygen-comprising gas may contain some steam. Steam acts as moderator gas in the gasification reaction. The ratio between oxygen and steam is preferably from 0 to 0.3 parts by volume of steam per part by volume of oxygen. The oxygen used is preferably heated before being contacted with the coal, preferably to a temperature of from about 200 to 500° C.

In order to achieve a more rapid and complete gasification, initial pulverisation of the solid carbonaceous feed is preferred. The partial oxidation reaction is preferably performed by combustion of a dry mixture of fine particulates of the carbonaceous feed and a carrier gas with oxygen in a suitable burner. Examples of suitable burners are described in U.S. Pat. No. 4,887,962, U.S. Pat. No. 4,523,529 and U.S. Pat. No. 4,510,874. When the feedstock is coal the term fine particulates is intended to include at least pulverized particulates having a particle size distribution so that at least about 90% by weight of the material is less than 90 μm and moisture content is typically between 2 and 8% by weight, and preferably less than about 5% by weight.

Steps (a) and (b) are preferably performed by feeding an oxygen-comprising gas and the carbonaceous feedstock to a burner firing into a combustion chamber at the upper end of the reactor vessel. Said reactor vessel is preferably provided with a quench chamber at the lower end of said vessel. The combustion chamber is fluidly connected to said quench chamber by a combustion chamber outlet opening. Step (c) is performed in said quench chamber. The walls of the combustion chamber are suitably cooled by indirect heat exchange between conduits through which a cooling medium flows and said wall. The wall itself may also be composed of said conduits. This type of wall is also referred to as a membrane wall.

The gasification chamber is preferably provided with one or more partial oxidation burners, wherein said burners are provided with supply means for a solid carbonaceous feed and supply means for an oxygen containing gas. The burners or burner may be directed downwards from the roof of the combustion chamber or fire horizontally or substantially horizontally. In the case of horizontal firing or substantial horizontal firing it is preferred to have pairs of diametrically-positioned burners. This results in a pair of two burners in a substantially opposite direction at the same horizontal position. The reactor may be provided with 1 to 5 of such pairs of burners, preferably 2 to 5 of such pairs. The upper limit of the number of pairs will depend on the size of the reactor. The firing direction of the pairs of burners may be slightly tangential as for example described in EP-A-400740.

Examples of suitable carrier gasses to transport the dry and solid feed to the burners are steam, nitrogen, synthesis gas and preferably carbon dioxide. Carbon dioxide is preferred because it achieves a better selectivity to synthesis gas and avoids build-up of nitrogen in downstream gas recycle streams. In step (c) the hot synthesis gas is cooled by direct contact of the gas with a liquid water-containing cooling medium. The direct contact is preferably achieved by injecting the liquid water-containing cooling medium into the gaseous stream of synthesis gas or by passing the synthesis gas through a batch of the liquid water-containing cooling medium, or combinations of said methods. More preferably step (c) is performed by injecting the liquid water-containing cooling medium as a spray into the synthesis gas as discharged into the quench chamber as described above. Alternatively the synthesis gas may flow through a diptube fluidly connected to the outlet opening of the combustion chamber and partly submerged in a water bath as present at the lower end of the quench chamber. In such a reactor it is preferred to cool the inner walls of the diptube by a stream of a liquid comprising the liquid water-containing cooling medium, which flows downwardly and along the inner wall of the diptube. Combinations of such diptube cooling and spraying are possible.

According to the invention, part or all of the liquid water-containing cooling medium is formed by water-rich by-product as obtained in step (e), that is being recycled to step (c), to form at least part of the liquid water-containing cooling medium. This water condensate is the water portion as obtained as by-product when performing step (e) and will typically contain water as the predominant component and water soluble compounds. These compounds are for example alcohols, carboxylic acids and other oxygenates. These compounds will at least in part decompose at the elevated temperature conditions when contacted with the hot synthesis gas. By using this water in this manner a costly and complicated waste water process for the water by-product of step (e) is avoided. In particular a significant concentration of methanol in the recycled liquid water-rich by-product can be accepted, such as 20 wt % or less, in particular 10 wt % or less, more in particular 5 wt % or less, even more in particular 2 wt % or less. The same advantageous upper concentration limits can apply to total oxygenates.

In one embodiment, the recycled liquid water-rich by-product contains at least 0.5 wt % of methanol, in particular at least 1 wt %, more in particular at least 2 wt %, even more in particular at least 5 wt %, still more in particular at least 8 wt %. Also, a concentration of dimethylether in the recycled liquid water-rich by-product can be accepted. In one embodiment, the recycled liquid water-rich by-product contains at least 0.1 wt % of dimethylether, in particular at least 0.5 wt %.

Overall, the recycled liquid water-rich by-product can contain at least 0.5 wt % oxygenates, in particular at least 1 wt %, more in particular at least 3 wt %, even more in particular at least 5 wt %, even more in particular at least 8 wt %, based on the total recycled liquid water-rich by-product. These oxygenates are not wasted by recycling in this manner.

The synthesis gas as obtained in step (c) may be submitted to an optional water scrubbing process step. Such a process step is well known and therefore not described in detail. The water scrubbing step generates a water stream containing solids, also referred to as black water.

In step (d) the gaseous stream as obtained in step (c) is shift converted by at least partially converting CO into $CO_2$, thereby obtaining a CO depleted stream. In this step the $H_2/CO$ ratio of the synthesis gas is increased from a lower level, typically below 1 and especially from between 0.3-0.6 for coal-derived synthesis gas to a higher value preferably above 1. The higher $H_2/CO$ ratio is preferred to perform step (e) in the most optimal manner. Stoichiometrically, two moles of $H_2$ and one mole of CO form one mole of methanol. The optimal $H_2/CO$ ratio for step (f) can be dependent on the type of catalyst used in step (f).

The water shift conversion reaction as performed in step (d) is well known in the art. Generally, water, usually in the form of steam, is mixed with the gaseous stream to form carbon dioxide and hydrogen. The catalyst used can be any of the known catalysts for such a reaction, including iron, chromium, copper and zinc. Copper on zinc oxide is a known shift catalyst.

The catalytic water shift conversion reaction of step (d) provides a hydrogen enriched, often highly enriched, synthesis gas, possibly having a $H_2/CO$ ratio above 3, more suitably above 5, preferably above 7, more preferably above 15, possibly 20 or even above.

In order to arrive at the desired $H_2/CO$ ratio for performing step (e) it is preferred to perform step (d) only on part of the gaseous stream obtained in step (c). In this preferred embodiment the scrubbed synthesis gas of step (c) is divided into at least two sub-streams, one of which undergoes step (d) to obtain a first CO depleted stream. This first CO depleted stream is combined with the second sub-stream to form a second CO depleted stream having the desired $H_2/CO$ ratio for performing step (e). Alternatively the cooled synthesis gas of step (c) may be split into at least two streams. Each stream is subjected to an optional scrubbing step separately. At least one stream is subjected to a step (d) to obtain a first CO depleted stream and at least one stream is not subjected to a step (d) to obtain the second sub-stream.

If desired one or more of the sub-stream(s) which are not subjected to step (d) could be used for other parts of the process rather than being combined with the converted sub-stream(s). Preferably part of such sub-stream is used for steam or power generation.

Hydrogen is preferably prepared from part of a CO depleted stream, more preferably from the first CO depleted stream. Hydrogen is preferably prepared in a Pressure Swing Adsorption (PSA) unit, a membrane separation unit or combinations of these. The hydrogen manufactured in this way can then be used as the hydrogen source in a possible further hydroprocessing step wherein the hydrocarbon products as made in step (e) are used as feed. This arrangement reduces or even eliminates the need for a separate source of hydrogen, e.g. from an external supply, which is otherwise commonly used where available.

The division of the gaseous stream as obtained in step (c) into sub-streams can be such so as to create any desired $H_2/CO$ ratio following their recombination. Any degree or amount of division is possible. Where the gaseous stream are divided into two sub-streams, the division into the sub-streams could be in the range 80:20 to 20:80 by volume, preferably 70:30 to 30:70 by volume, depending upon the desired final $H_2/CO$ ratio. Simple analysis of the $H_2/CO$ ratios in the second CO depleted stream and knowledge of the desired ratio for subsequent process steps, in particular step (e), allows easy calculation of the division.

The simple ability to change the degree of division into the sub-streams also provides a simple but effective means of accommodating variation in the $H_2/CO$ ratio in the gaseous stream as obtained in step (c) which variations are primarily due to variation in feedstock quality. With feedstock quality is here meant especially the hydrogen and carbon content of the original carbonaceous feedstock, for example, the 'grade' of coal. Certain grades of coal generally having a higher carbon content will, after gasification of the coal, provide a greater production of carbon monoxide, and thus a lower $H_2/CO$ ratio. However, using other grades of coal means removing more contaminants or unwanted parts of the coal, such as ash and sulphur and sulphur-based compounds. The ability to change the degree of division of the synthesis gas stream into the sub-streams allows the process to use a variety of feedstocks, especially 'raw' coal, without any significant re-engineering of the process or equipment to accommodate expected or unexpected variation in such coals.

Preferably, after step (d) an additional step of separating sulphur compounds, carbon dioxide and other possible impurities from the shifted gas to obtain a purified synthesis gas effluent, is performed, and step (e) uses the purified synthesis gas effluent for the oxygenate synthesis.

Suitably the synthesis gas is subjected to a $CO_2$ recovery system thereby obtaining a $CO_2$ rich stream and a $CO_2$ poor stream and wherein the $CO_2$ poor stream is used in step (e). The $CO_2$ rich stream may be used as the $CO_2$ containing transport gas in step (a).

In one embodiment it is preferred to remove part of the $CO_2$ as is present in the synthesis gas intended for use in step (e). Part of the $CO_2$ is preferably used in step (a) in an embodiment wherein $CO_2$ is used as carrier gas. Excess $CO_2$ is preferably stored in subsurface reservoirs or used more preferably for enhanced oil or gas recovery or enhanced coal bed methane recovery. Excess $CO_2$ may also be sequested by mineral carbonation such as for example described in WO-A-02/085788.

The $CO_2$ recovery system is preferably a combined carbon dioxide/hydrogen sulfide removal system, preferably wherein the removal system uses a physical solvent process. The $CO_2$ recovery may be performed on the CO-depleted stream or alternatively on the second CO-depleted stream. More preferably the $CO_2$ recovery from the sub-stream, which stream is not being subjected to step (d), is performed separately from the $CO_2$ recovery from the first CO depleted stream before said streams are combined.

On an industrial scale there are chiefly two categories of absorbent solvents, depending on the mechanism to absorb the acidic components: chemical solvents and physical solvents. Each solvent has its own advantages and disadvantages as to features as loading capacity, kinetics, regenerability, selectivity, stability, corrosivity, heat/cooling requirements etc.

Chemical solvents which have proved to be industrially useful are primary, secondary and/or tertiary amines derived alkanolamines. The most frequently used amines are derived from ethanolamine, especially monoethanol amine (MEA), diethanolamine (DEA), triethanolamine (TEA), diisopropanolamine (DIPA) and methyldiethanolamine (MDEA).

Physical solvents which have proved to be industrially suitable are cyclo-tetramethylenesulfone and its derivatives, aliphatic acid amides, N-methylpyrrolidone, N-alkylated pyrrolidones and the corresponding piperidones, methanol, ethanol and mixtures of dialkylethers of polyethylene glycols.

A well-known commercial process uses an aqueous mixture of a chemical solvent, especially DIPA and/or MDEA, and a physical solvent, especially cyclotetramethylene-sulfone. Such systems show good absorption capacity and good selectivity against moderate investment costs and operational costs. They perform very well at high pressures, especially between 20 and 90 bara.

The physical absorption process is preferred and is well known to the man skilled in the art. Reference can be made to e.g. Perry, Chemical Engineerings' Handbook, Chapter 14, Gas Absorption. The liquid absorbent in the physical absorption process is suitably methanol, ethanol, acetone, dimethylether, methyl i-propyl ether, polyethylene glycol or xylene, preferably methanol. This process is based on carbon dioxide and hydrogen sulfide being highly soluble under pressure in the methanol, and then being readily releasable from solution when the pressure is reduced as further discussed below. This high pressure system is preferred due to its efficiency, although other removal systems such as using amines are known. The physical absorption process is suitably carried out at low temperatures, preferably between $-60°$ C. and $0°$ C., preferably between $-30$ and $-10°$ C.

The physical absorption process is carried out by contacting the light products stream in a counter-current upward flow with the liquid absorbent. The absorption process is preferably carried out in a continuous mode, in which the liquid absorbent is regenerated. This regeneration process is well known to the man skilled in the art. The loaded liquid absorbent is suitably regenerated by pressure release (e.g. a flashing operation) and/or temperature increase (e.g. a distillation process). The regeneration is suitably carried out in two or more steps, preferably 3-10 steps, especially a combination of one or more flashing steps and a distillation step.

The regeneration of solvent from the process is also known in the art. Preferably, the present invention involves one integrated solvent regeneration tower. Further process conditions are for example described in DE-A-2610982 and DE-A-4336790.

Preferably the synthesis gas is subjected to one or more further removal systems prior to using said stream in step (e). These removal systems may be guard or scrubbing units, either as back-up or support to the $CO_2/H_2S$ removal system, or to assist in the reduction and/or removal of other contaminants such as HCN, $NH_3$, COS and $H_2S$, metals, carbonyls, hydrides or other trace contaminants.

In step (e) an oxygenate synthesis using the synthesis gas effluent of step (d) is performed, to obtain a methanol and/or dimethylether containing oxygenate effluent and a first liquid water-rich by-product.

Step (e) can be or include a syngas to methanol conversion process. This can be any methanol synthesis process, in particular any conventional methanol synthesis process, including e.g. batch processes and, preferably, continuous processes.

In general, methanol synthesis can be described by the following reactions:

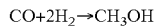

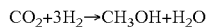

By the second reaction, in particular when the syngas contains $CO_2$, water is produced as by-product in the methanol-containing effluent, which is suitably separated. According to the present invention, this separation does not need to be conducted to achieve high water purity, since residual methanol in the separated water can advantageously be recycled to step (c) of the process. The water is also referred to as third liquid water-rich by-product in the present description and claims.

Such a process is for example described in WO 2006/020083, incorporated by reference, in particular in paragraphs [0069] to [0086]. As stated there, the syngas input to the methanol synthesis reactor suitably has a molar ratio of hydrogen ($H_2$) to carbon oxides ($CO+CO_2$) in the range of from about 0.5:1 to about 20:1, preferably in the range of from about 2:1 to about 10:1. In another embodiment, the syngas has a molar ratio of hydrogen ($H_2$) to carbon monoxide (CO) of at least 2:1. In a further embodiment of the present invention the molar ratio is in the range from about 1:1 to about 10:1. Carbon dioxide is optionally present in an amount of not greater than 50% by weight, based on total weight of the syngas.

Also as stated there, the stoichiometric molar ratio is sufficiently high so as maintain a high yield of methanol, but not so high as to reduce the volume productivity of methanol. Preferably, the syngas fed to the methanol synthesis has a stoichiometric molar ratio (i.e., a molar ratio of H2:(2CO+3CO$_2$)) of from about 1.0:1 to about 2.7:1, more preferably from about 1.1 to about 2.0, more preferably a stoichiometric molar ratio of from about 1.2:1 to about 1.8:1.

The syngas can contain $CO_2$ and CO at a molar ratio of from about 0.5 to about 1.2, preferably from about 0.6 to about 1.0.

WO 2006/020083 moreover states suitable catalysts, refers to suitable processes for making methanol synthesis catalysts, states suitable temperature and pressure ranges for a methanol synthesis process, as well as suitable gas hourly space velocities for a continuous process, all incorporated herein by reference.

WO 2006/020083 also discusses refining of crude methanol to make a methanol product, in paragraphs [0087]-[0094], incorporated herein by reference. As important element of the refining is the removal of by-product water from this process, as already discussed above. With reference to FIG. 1 of WO 2006/020083, the synthesis of methanol from syngas stream 106, which can be obtained in accordance with the present invention from a solid carbonaceous feedstock, and the refining in a separation zone is discussed on page 29 line 8-page 30 line 13, incorporated herein by reference. The water stream 118 in FIG. 1 can be used as water-rich by-product that is recycled to step c), to form at least part of the liquid water-containing cooling medium.

The methanol thus produced can form the oxygenate effluent from step (e). In a preferred embodiment, the oxygenate effluent as prepared comprises dimethylether, preferably at least 0.1 mol % of the oxygenates therein, more preferably at least 0.3 mol %. To this end step (e) of the process preferably contains a step of converting methanol and/or syngas to dimethylether.

Processes to convert syngas and/or methanol to dimethylether are discussed in WO 2006/020083, in particular in section III., incorporated herein by reference. Dimethylether can be produced directly from syngas; or in a two-step process from methanol first produced from syngas, or from methanol and syngas together. Along all routes, a water-containing by-product is produced which can be recycled to step (c) according to the present invention, wherein it is acceptable that methanol and/or dimethylether are contained in the recycle stream.

In a preferred embodiment, in a first step, (e1), of step (e), at least part of the synthesis gas effluent is converted to a methanol containing effluent and a second liquid water-rich by-product (such as described hereinabove), and then, in step (e2), at least part of the methanol containing effluent is converted to a dimethylether containing effluent and a third liquid water-rich by-product. The second and third liquid water-rich by-products form part of the first liquid water-rich by-product as defined above, wherein preferably at least part of the first water-rich by-product is recycled to step (c).

In an especially preferred embodiment at least part of the third liquid water-rich by-product is recycled to step (c), and this can be the only water-containing by-product stream from steps (e).

The conversion of methanol to dimethylether is known in the art. This conversion is an equilibrium reaction. In the conversion the alcohol is contacted at elevated temperature with a catalyst. In EP-A 340 576 a list of potential catalysts are described. These catalysts include the chlorides of iron, copper, tin, manganese and aluminium, and the sulphates of copper, chromium and aluminium. Also oxides of titanium, aluminium or barium can be used. Preferred catalysts include aluminium oxides and aluminium silicates. Alumina is particularly preferred as catalyst, especially gamma-alumina. Although the methanol may be in the liquid phase the process is preferably carried out such that the methanol is in the vapour phase. In this context the reaction is suitably carried out at a temperature of 140 to 500° C., preferably 200 to 400° C., and a pressure of 1 to 50 bar, preferably from 8-12 bar. In view of the exothermic nature of the conversion of methanol to dimethylether the conversion of step (a) is suitably carried out whilst the reaction mixture comprising the first catalyst is being cooled to maximise dimethylether yield.

The ratio of dimethylether and methanol in the product stream (dimethylether containing effluent) of step (e2) may vary between wide ranges. Suitable ranges include a dimethylether to methanol weight ratio of 0.5:1 to 100:1, preferably from 2:1 to 20:1. Suitably the reaction is led to equilibrium. This includes that the dimethylether to methanol weight ratio may vary from 2:1 to 6:1. Evidently, the skilled person may decide to influence the equilibrium by applying different reaction conditions and/or by adding or withdrawing any of the reactants.

Preferably step (e2) of the process according the invention is performed by converting methanol into dimethylether over a first catalyst, to yield a dimethylether product stream containing methanol, alcohol, dimethylether and water, adding a non-volatile base to the dimethylether product stream and separating the dimethylether product stream into a vaporous dimethylether-rich stream and a liquid water-containing stream, i.e. the third liquid water-rich by-product, which water-containing stream comprises at most 5% wt of methanol, based on the total weight of water and methanol.

Applicants have found that the vaporous dimethyl ether stream is very suited to be used as feed to a process wherein the vaporous dimethylether-rich stream is converted to an olefin over a second catalyst.

Applicants found that by allowing a relatively small amount of methanol in the liquid water-containing stream the separation described above can be simple. The majority of unconverted methanol is entrained with the vaporous dimethylether-rich stream. This is not disadvantageous if such a stream is used as feed to a process to prepare an olefin. Since no high purity in dimethylether of the vaporous dimethylether-rich stream is required a simple separation such as a cheap distillation or flash is sufficient.

In addition, this process provides an elegant solution to get rid of by-products, that are formed in the production of dimethylether from methanol, by removal with the liquid water-containing stream. In particular the enrichment of the dimethylether product stream with a base forms products, in particular neutralization products, which can be removed with the water-containing stream. This water containing stream is advantageously used as the third liquid water-rich by-products in the process according to the present invention. The presence of a base in said third liquid water rich by-product is advantageous to neutralise any acids as present in the stream of hot synthesis gas as prepared in step (b).

In the present process, the purity of the dimethylether product separation of the dimethylether product is not a major concern, neither is odor nuisance. However, it was found that by adding a base to all or part of the dimethylether-rich product stream, by-products from the methanol to dimethylether conversion can be effectively bound and removed with the water-rich phase, which are harmful in the downstream conversion to olefins, in particular corrosive components such as carboxylic acids.

Preferably methanol is used having a purity of at least 99% w, preferably at least 99.5% w, based on the total weight of the reactants that are converted over the first catalyst, so that the dimethylether is substantially pure dimethylether.

Advantageously a pH of at least 7 is maintained in the hot dimethylether product stream, in particular in a liquid water-containing fraction of the dimethylether product stream. This stream is enriched with a base to this end. In order to enrich the dimethylether product stream with a base, the base is suitably contacted with or added to the dimethylether product stream, such that a pH of from 7 to 12 is achieved in the resulting liquid water-containing fraction of the dimethylether product stream. Such a base can be sodium or potassium hydroxide, or any other alkali metal or alkaline earth metal bases or mixtures thereof, optionally dissolved in water. The base may be added to the hot dimethylether product stream or in any preceding stream.

In the process of the present invention the dimethylether product stream conveniently has a temperature of 200 to 400° C. In order to facilitate the separation of step b) the dialkyl product stream may be cooled. This may be achieved by flashing. However, suitably, the heat of this product stream is used to increase the temperature of the dimethylether that is to be used in the subsequent preferred olefins manufacture process, e.g., by heat exchange.

The ratio of dimethylether and methanol in the dimethylether product stream may vary between wide ranges. Suitable ranges include a dimethylether to methanol weight ratio of 0.5:1 to 100:1, preferably from 2:1 to 20:1. Suitably the reaction is led to equilibrium. This includes that the dimethylether to methanol weight ratio may vary from 2:1 to 6:1. Evidently, the skilled person may decide to influence the equilibrium by applying different reaction conditions and/or by adding or withdrawing any of the reactants.

The dimethylether product stream may be separated in a simple separation unit, e.g., in a fractionation column. Since the methanol is a valuable product and since it may react in the olefins manufacture step, the separation of the gas-liquid mixture yields a liquid water-containing stream and a vaporous dimethylether-rich stream, wherein the majority of the methanol is contained in the vaporous dimethylether-rich stream. Therefore, the liquid water-containing stream contains at most 5% wt, preferably, at most 3% wt, more preferably at most 1% wt of alkyl alcohol, based on the total of water and alkyl alcohol. It is within the skill of the artisan to determine the correct conditions in a fractionation column to arrive at such a separation. He may choose the correct conditions based on, i.a., fractionation temperature, pressure, trays, reflux and reboiler ratios. The conditions are most preferably chosen such that the liquid-water stream contains insignificant amounts of methanol. Since water is normally produced in the olefins manufacture step it is not required to remove all water from the dimethylether-rich stream. The dimethylether-rich stream suitably contains at most 5% wt, preferably at most 1% wt of water, based on the total weight of water, methanol and dimethylether. The dimethylether product stream is preferably separated into the vaporous dimethylether-rich stream having a temperature of 75 to 140° C., and the liquid water-containing stream having a temperature of 80 to 175° C.

An alternative suitable route to produce dimethylether from methanol is described in the paper "Dehydration of methanol to dimethylether by catalytic distillation", An, W. et al., Canadian Journal of Chemical Engineering (2004), vol. 82, p. 948-955 or in WO-A-2007/014534.

Other suitable processes to convert syngas to methanol and/or dimethylether are described in e.g. US2007/0203380A1 and US2007/0155999A1.

The invention is also directed to a process to prepare an olefin-containing product or a gasoline product from a solid carbonaceous feedstock by performing the process as described above to obtain a methanol- and/or dimethylether-containing oxygenate effluent and converting the oxygenate effluent to an olefin-containing product or a gasoline product and a fourth liquid water-rich by-product in a step (f). Preferably at least part of the fourth liquid water-rich by-product is used in step (c), forming at least part of the liquid water-containing cooling medium.

In step (f) the oxygenate effluent from step (e) may be converted to an olefin-containing product and a second liquid water-rich by-product. The olefins manufacture from oxygenates, in particular methanol and/or dimethylether is known in the art. Suitable processes to convert a dimethylether-containing feedstock to light olefins are for example are described in WO 2006/020083, section IV. Preferred processes include processes for making an olefin product from an oxygenate effluent, comprising providing a silicoaluminophosphate molecular sieve having catalytic sites within the molecular sieve and contacting the sieve with the oxygenate effluent under conditions effective to produce an olefin product as described in WO-A-0074848, which publication is incorporated herein by reference. The liquid-rich by-product obtained in such a process is referred to as the fourth liquid water-rich by-product. Preferably at least part of the fourth liquid rich by-product is used in step (c), forming at least part of the liquid water-containing cooling medium.

Processes to convert an oxygenate effluent to a gasoline type product are well known. A known example is the ExxonMobil Methanol to Gasoline (MTG) Process. For example WO-A-0129152 describes a process for selectively converting the oxygenate effluent to normally liquid boiling range C5+ hydrocarbons in a single step. The process comprises, contacting the feed under oxygenate conversion conditions with a catalyst comprising a unidimensional 10-ring zeolite, e.g., one selected from the group consisting of ZSM-22, ZSM-23, ZSM-35, ZSM-48, ZSM-57, and ferrierite, at temperatures below 350° C. and oxygenate pressures above 40 psia (276 kpa); and recovering a normally liquid boiling range C5+ hydrocarbons-rich product stream, for example gasoline. The liquid rich by-product obtained in such a process is referred to as the fourth liquid water-rich by-product. Preferably at least part of the fourth liquid rich by-product is used in step (c), forming at least part of the liquid water-containing cooling medium.

Further details of the invention will now be described with reference to the drawings.

Same reference numbers as used below refer to the same or similar structural elements.

Reference is made to FIG. 1. FIG. 1 schematically shows a system 1 for producing synthesis gas. In a gasification reactor 2 a carbonaceous stream and an oxygen containing stream may be fed via lines 3, 4, respectively. FIG. 1 shows a pair of burners 5 firing horizontally into a combustion chamber 6 at the upper end of the reactor 2 and a quench chamber 7 at the lower end of the reactor 2 fluidly connected by a combustion chamber outlet opening 8. The outlet opening 8 is fluidly connected to a diptube 9. Diptube 9 is provided with spray nozzles fluidly connected to a cooling water supply 17B. Diptube 9 is partly submerged in a water bath 11 as present at the lower end of the quench chamber 7. The inner walls of the diptube 9 are cooled by a stream of a liquid water cooling medium comprising as discharged like a waterfall from circular opening 12. The liquid water-containing cooling medium for this waterfall is supplied via distributor 13. Distributor 13 in turn being supplied by cooling water supply 17A.

The solid carbonaceous feed is at least partially oxidised in the gasification reactor 2, thereby obtaining a synthesis gas and a slag. The slag drops down into the water bath 11 and is drained through slag sluicing device 14 for further processing. An example of a slag sluicing device is described in EP-B-1224246, which reference is hereby incorporated by reference.

As shown in the embodiment of FIG. 1, the cooled synthesis gas leaving the quench chamber 7 is fed via line 15 to a wet gas scrubber 16. Part of the scrubbed gas is subsequently fed via line 18A to a shift converter 19 to react at least a part of the water with CO to produce $CO_2$ and $H_2$, thereby obtaining a CO-depleted stream in line 20. Waste water from gas scrubber 16 is removed via line 22 and optionally partly recycled to the gas scrubber 16 via line 23. Fresh water for scrubber 16 may be recycled water-rich by-product supplied via line 17C.

Further improvements are achieved when the raw synthesis gas in line 18A is heated in a heat exchanger 21 against the shift converted synthesis gas in line 18A that is leaving the shift converter 16.

The CO depleted stream in line 20 can be fed to a carbon dioxide and/or hydrogen sulphide removal system 21A. The remaining scrubbed synthesis gas 18B, which gas bypasses the shift reactor 19, is fed to a carbon dioxide and/or hydrogen sulphide removal system 21B. The treated gas 24 is combined with the shifted and treated synthesis gas 25, to obtain a combined synthesis gas effluent 26 having a modified hydrogen to carbon monoxide molar ratio as feedstock for oxygenate synthesis unit 100.

In the embodiment of the oxygenate synthesis unit 100 shown, the synthesis gas effluent from line 26 is first converted in the methanol synthesis unit 101 to a methanol-containing effluent in line 103 and a second water-containing by-product, which is separated in the unit 101 and removed as stream 102. The methanol-containing effluent in line 103 may be further processed to obtain methanol as a product 104 or may be, at least partly, converted to dimethylether in the prereactor unit 105, which may also form part of the oxygenate synthesis unit 100. Water is formed in this reaction in prereactor unit 105, which is separated in the unit 105, and a third liquid water-rich by-product stream 107 is removed. The stream 108 contains dimethylether and typically some methanol, as well as some water. The main function of the prereactor 105 is to lower the water load on an optional downstream process, such as an oxygenate-to-olefins process. Since further water will be formed in such a downstream process, a high purity in oxygenates in stream 108 is not needed. A simple separation of the bulk of water from the prereactor effluent may be sufficient. This is also true for the third water-containing by-product stream 107, which is preferably recycled via line 17 in accordance with the present invention. Oxygenates still contained in this water stream are retained within the process and not wasted. The second and third water-containing by-product streams 102 and 107 together form the first water-containing by-product stream. Either one or both streams 102 and 107 can be recycled partly or fully via line 17 to the quench chamber 7.

Figure 2:
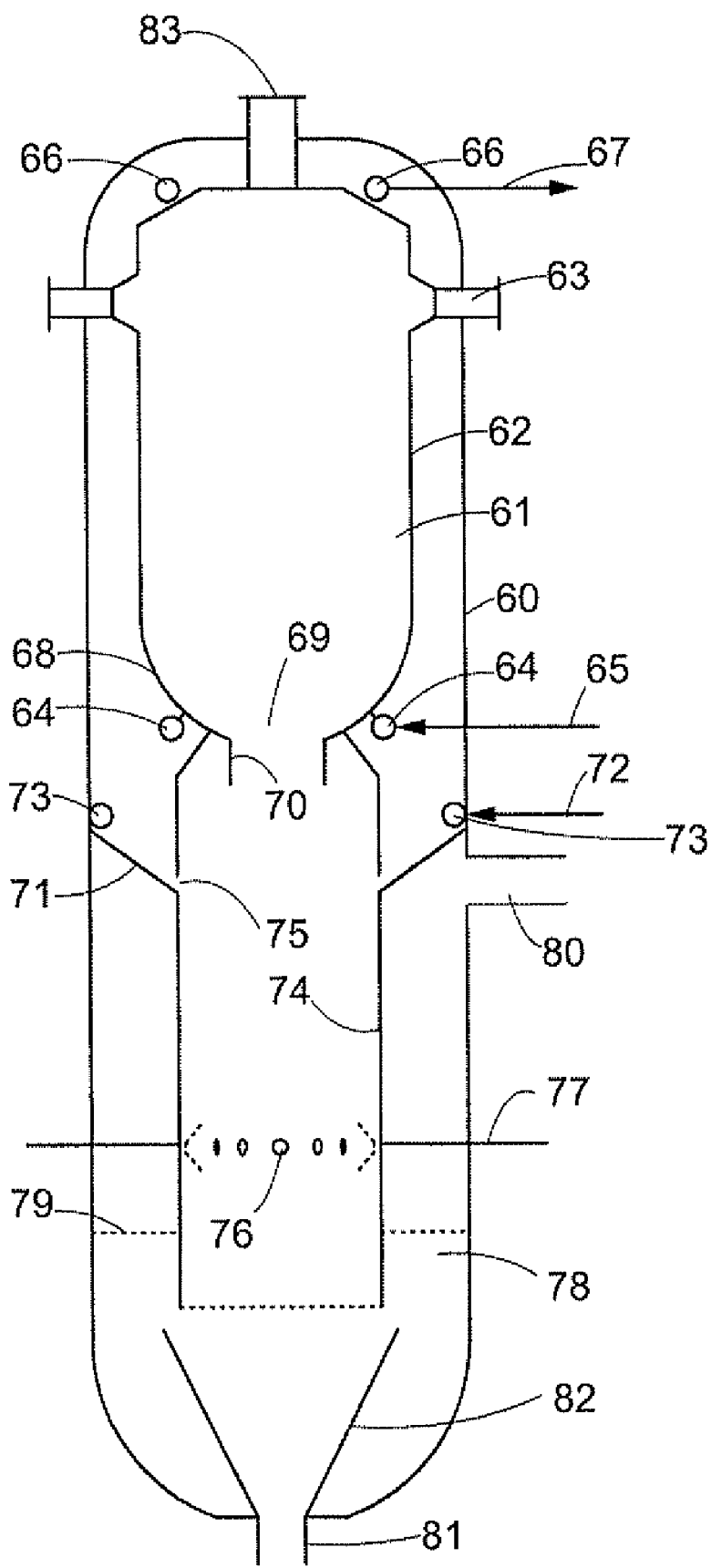
FIG. 2 shows schematically a longitudinal cross-section of a gasification reactor of FIG. 1.

FIG. 2 shows a longitudinal cross-section of a gasification reactor 2 of FIG. 1 with somewhat more details. The reference of FIG. 2 refer to the same elements as described when discussing FIG. 1 above. FIG. 2 shows a gasification reactor 60 wherein a cooling section is part of the gasification reactor as will be described below. Reactor 60 is provided with a gasification chamber 61 as defined by a so-called membrane wall 62. Gasification chamber 61 is provided with one or more pairs of diametrically-opposed burners 63. The membrane wall is composed of vertical conduits, which are fixed together and in which, in use, a cooling medium, i.e. evaporating water, flows from a distributor 64 to a steam header 66. Distributor 64 is provided with a cooling medium supply line 65 and steam header 66 is provided with a steam discharge conduit 67. At the lower end of the tubular membrane wall a diverging frusto-conical part 68 is attached. At the lower opening 69 of said part 68 a tubular part 70, extending downwards, is provided to guide the slag and synthesis gas into a diptube 74. By having an opening 69, which is smaller than the diameter of diptube 74, one intends to avoid as much as possible that slag particles contact the inner walls of the diptube 74.

The inner walls of diptube 74 are wetted by a downwardly-moving layer of water. This layer of water is achieved by introducing water via supply ring 73. The introduced water will flow via a sloped plane 71 to circular opening 75 and further downwards along the inner wall of diptube 74.

Step (c) of the process according to the present invention is performed by introducing the liquid water-containing cooling medium via supply conduit 77, corresponding to 17B in FIG. 1, and nozzles 76 into the flow of synthesis gas. Step (c) is preferably performed by supplying the liquid water-containing cooling medium distributor 72 via supply conduit 72, corresponding to 17A in FIG. 1. In this manner the inner walls of the diptube 74 are cooled by a waterfall like stream of the liquid water cooling medium as discharged from circular opening 75. Because the temperature of the synthesis gas at the location of opening 75 is still high decomposition of the oxygenates as present in the cooling medium is most likely.

FIG. 2 further shows a water bath 78 having a surface 79. Through this water bath 78 synthesis gas will be further cooled. The cooled synthesis gas is discharged from the reactor 60 via outlet 80. Slag particles are guided via cone 82 to outlet 81. Reference number 83 may be a start-up burner or a manhole.

Figure 3:
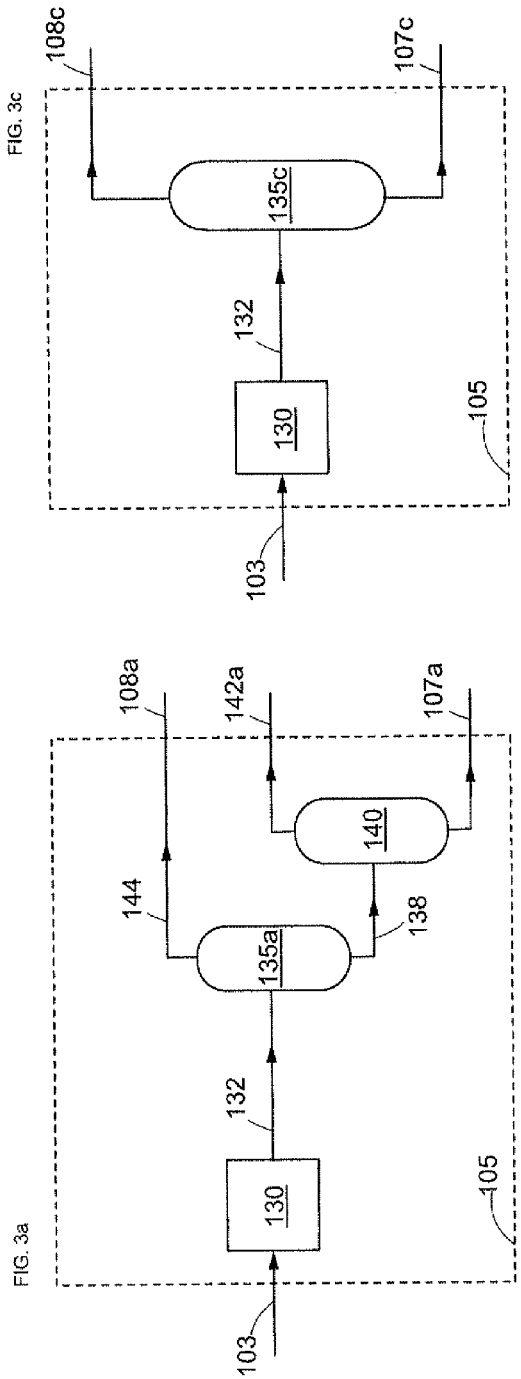
FIG. 3 a,b,c,d shows schematically various embodiments of the prereactor unit of FIG. 1.
Figure 3:
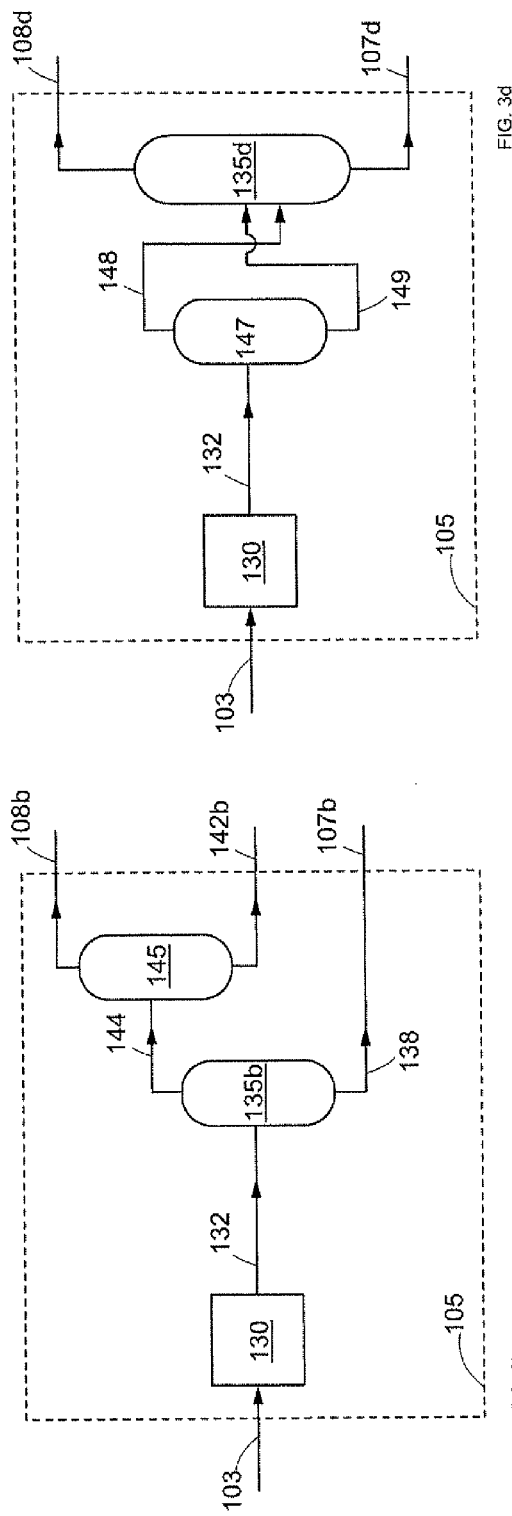

In FIG. 3, several embodiments of the prereactor unit 105 of FIG. 1 are schematically shown. Turning first to FIG. 3a, the methanol-containing effluent in line 103 is at least partly converted to dimethylether in the prereactor 130, and effluent in line 132 is fed to first separation unit or column 135a, which can be a fractionation/distillation column, that produces an first stream 108a rich in dimethylether, and optionally containing some methanol and a relatively low amount of water, and a bottom stream 138. The bottom stream is fed to a second separation unit 140, which can also be a distillation column, to produce a methanol-rich stream 142a and a water-rich bottom stream 107a.

In FIG. 3b, the first separation unit 135b is operated such that a water-rich stream 107b of sufficient quality is obtained right away, and the overhead stream 144 rich in dimethylether and containing the majority of the methanol is separated in second separation unit 145, to obtain a stream 108b rich in dimethylether, and a methanol-rich stream 142b.

The streams 142a and 142b in FIGS. 3a and 3b can e.g. be, fully or in part, recycled to the inlet of unit 105, or sent to unit 101, or even sent as recycle stream to line 17.

In a two-stage separation as in FIGS. 3a and 3b a fairly good separation between the three main components can be achieved. The water-rich stream in line 107a,b can contain less than 1 wt % of oxygenate, even less than 0.5 wt %, such as less than 0.2 wt %.

The embodiment of FIG. 3c is simpler in that only one separation unit 135c is arranged. Suitably this unit is operated such that, next to dimethylether-rich stream 108c, a water-rich stream 107c containing a sufficiently low amount of methanol and/or DME is obtained, so that it can economically be recycled to line 17. The oxygenate content will typically be higher than in the two stage embodiments discussed before, such as between 0.5 wt and 20 wt %, or between 1 wt % and 18 wt %, or between 5 wt % and 15 wt %. Recycling in this way in accordance with the invention simplifies the separation of the effluent from the DME prereactor without wasting valuable oxygenates.

The embodiment of FIG. 3d is a variant of 3c. Prior to the single separation unit 135d, the effluent 132 is sent to a flash vessel 147. In the flash vessel 147 the pressure is reduced and the product stream is cooled to below the dew point of water. The vaporous effluent from the flash vessel 147 comprises most of the dimethylether and some methanol, and leaves the flash vessel via a line 148. The liquid effluent, comprising water and methanol, leaves the flash vessel 147 via a line 149. The effluents from lines 148 and 149 are both fed into a fractionation column 135d, whereby line 149 debouches into the fractionation column 135d at a point above the location where line 148 debouches into column 135d. In fractionation column 135d the gas-liquid mixture, obtained from both streams, is separated into a liquid-rich stream 107d comprising water and less than 1% wt methanol, based on the total of water and methanol, and a vaporous dimethylether-rich stream 108d, comprising dimethylether, the majority of the methanol and typically some water.

The invention claimed is:

1. A process to prepare methanol and/or dimethylether from a solid carbonaceous feedstock comprising the steps of
    (a) feeding an oxygen-comprising gas and the carbonaceous feedstock to a burner firing into a reactor vessel,
    (b) performing a partial oxidation of the carbonaceous feedstock in said burner to obtain a stream of hot synthesis gas and a liquid slag whereby both the hot synthesis gas and the liquid slag flow downwardly relative to the burner,
    (c) cooling the hot synthesis gas by direct contact with a liquid water-containing cooling medium,
    (d) performing a water shift reaction on at least part of the synthesis gas, to obtain a synthesis gas effluent,
    (e) performing an oxygenate synthesis using the synthesis gas effluent of step (d), to obtain a methanol and/or dimethylether containing oxygenate effluent and a first liquid water-rich by-product,
    wherein at least part of the first liquid water-rich by-product is used in step (c), forming at least part of the liquid water-containing cooling medium.

2. The process according to claim 1, wherein step (e) comprises the steps of
    (e1) converting at least part of the synthesis gas effluent to a methanol containing effluent and a second liquid water-rich by-product;
    (e2) converting at least part of the methanol containing effluent to a dimethylether containing effluent and a third liquid water-rich by-product,
    wherein the second and third liquid water-rich by-products form part of the first liquid water-rich by-product.

3. The process according to claim 2, wherein step (e2) is performed by converting methanol into dimethylether over a first catalyst, to yield a dimethylether product stream containing methanol, alcohol, dimethylether and water, adding a base to the dimethylether product stream and separating the dimethylether product stream into a vaporous dimethylether-rich stream and a liquid water-containing stream as the third liquid water-rich by-product, which water-containing stream comprises at most 5% wt of methanol, based on the total weight of water and methanol.

4. The process according to claim 2, wherein at least part of the second water-rich by-product is recycled to step (c).

5. The process according to claim 2, wherein at least part of the third liquid water-rich by-product is recycled to step (c).

6. The process according to claim 1, wherein the recycled liquid water-rich by-product contains at least 1 wt % oxygenates based on the total recycled liquid water-rich by-product.

7. The process according to claim 1, wherein the recycled liquid water-rich by-product contains at least 3 wt % oxygenates based on the total recycled liquid water-rich by-product.

8. The process according to claim 1, wherein the recycled liquid water-rich by-product contains at least 5 wt % oxygenates based on the total recycled liquid water-rich by-product.

9. The process according to claim 1, wherein sulphur compounds, carbon dioxide and other possible impurities are separated from the shifted gas as obtained in step (d) to obtain a purified synthesis gas.

10. The process according to claim 1, wherein step (b) is performed by feeding an oxygen-comprising gas and the carbonaceous feedstock to a burner firing into a combustion chamber at the upper end of the reactor vessel and a quench chamber at the lower end of the reactor vessel fluidly connected by a combustion chamber outlet opening and wherein step (c) is performed in said quench chamber.

11. The process according to claim 10, wherein step (c) is performed by injecting the liquid water-containing cooling medium as a spray into the synthesis gas as discharged into the quench chamber.

12. The process according to claim 10, wherein the synthesis gas flows through a diptube fluidly connected to the outlet opening of the combustion chamber and partly submerged in a water bath as present at the lower end of the quench chamber, wherein the inner walls of the diptube are cooled by a stream of a liquid comprising the liquid water-containing cooling medium which flows downwardly and along the inner wall of the diptube.

13. The process according to claim 1, wherein the liquid water-containing cooling medium as used in step (c) has a temperature of at most 50° C. below the bubble point temperature of water at the pressure of the hot synthesis gas.

14. The process according to claim 1, wherein only part of the synthesis gas is subjected to step (d) and wherein the remaining synthesis gas, which gas by-passes step (d), is combined with the shifted synthesis gas, to obtain a combined synthesis gas effluent having a modified hydrogen to carbon monoxide molar ratio as feedstock for step (e).

* * * * *